US012622985B2

(12) United States Patent
Kida et al.

(10) Patent No.: US 12,622,985 B2
(45) Date of Patent: May 12, 2026

(54) STERILIZATION METHOD FOR MEDICAL RUBBER PART

(71) Applicant: Sumitomo Rubber Industries, Ltd., Kobe (JP)

(72) Inventors: Yogun Kida, Kobe (JP); Kei Tajima, Kobe (JP); Kazuki Nojiri, Kobe (JP); Yuichiro Matsutani, Kobe (JP); Shumpei Morita, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 384 days.

(21) Appl. No.: 18/382,182

(22) Filed: Oct. 20, 2023

(65) Prior Publication Data

US 2024/0189463 A1 Jun. 13, 2024

(30) Foreign Application Priority Data

Oct. 21, 2022 (JP) ................................ 2022-169472

(51) Int. Cl.
*A61L 2/081* (2026.01)
*A61L 103/00* (2026.01)

(52) U.S. Cl.
CPC .......... *A61L 2/081* (2013.01); *A61L 2103/23* (2026.01)

(58) Field of Classification Search
CPC ............................ A61L 2/081; A61L 2103/23
See application file for complete search history.

(56) References Cited

U.S. PATENT DOCUMENTS

2017/0197024 A1* 7/2017 Kiminami ................. A61J 1/05
2017/0233124 A1* 8/2017 Fournier ................ B65B 31/00
53/425

FOREIGN PATENT DOCUMENTS

CA 2254696 A1 * 6/1999 ........... A61L 31/048
ES 2545204 T3 * 9/2015 ......... B65D 39/0023
JP 2002-301133 A 10/2002
JP 2017-531604 A 10/2017

OTHER PUBLICATIONS

English translation ES-2545204-T3 (Year: 2015).*
English translation of CA-2254696-A1 (Year: 1999).*

* cited by examiner

*Primary Examiner* — Sean E Conley
(74) *Attorney, Agent, or Firm* — XSENSUS LLP

(57) ABSTRACT

A sterilization method for a medical rubber part is a sterilization method for a medical rubber part that can include a body made from an elastic material and that can include an inactive resin film stacked on at least a portion of a surface of the body, where the sterilization method can include irradiating a packaging article with gamma ray, the packaging article accommodating a plurality of the medical rubber parts and having an oxygen concentration not higher than 5%.

15 Claims, 7 Drawing Sheets

STERILIZATION METHOD FOR MEDICAL RUBBER PART

CROSS-REFERENCE TO RELATED APPLICATION(S)

The present application claims priority to Japanese patent application JP 2022-169472, filed on Oct. 21, 2022, the entire contents of which is incorporated herein by reference in its entirety.

BACKGROUND

Field

The present disclosure relates to a sterilization method for a medical rubber part.

Background Art

Medical rubber plugs for tightly closing openings of syringes, vials, and the like may be required to have many characteristics such as non-eluting characteristics, high cleanability, chemical resistance, resistance to needle piercing, self-sealability, and high slidability. Quality characteristics that may be required of the medical rubber plugs may be required, in terms of use of the medical rubber plugs, to comply with the regulations stipulated in "Test for Rubber Closure for Aqueous Infusions" of the 17th edition of the Japanese Pharmacopoeia, as an example.

There is an increasing demand for medical rubber products (syringe gaskets, vial plugs, and the like) to be delivered in a state of guaranteeing sterilization thereof, i.e., to be ready-to-use (RTU). As methods for guaranteeing sterilization, there are methods involving sterilization with high-pressure steam, sterilization with ethylene oxide gas (EOG), and sterilization with gamma ray. The method involving sterilization with gamma ray may have an advantage that a medical rubber product can be sterilized in a state of being packaged and thus can be delivered without opening the package. Meanwhile, the method involving sterilization with EOG may have environment-related issues. In view of this, the method for guaranteeing sterilization tends to be switched to the method involving sterilization with gamma ray.

The method involving sterilization with gamma ray may guarantee sterilization by means of absorbed dose setting and actually measured values. If a plurality of medical rubber parts are put into a packaging bag and sterilization with gamma ray is performed, unevenness among the medical rubber parts might occur in the packaging bag. Thus, even when the packaging bag is irradiated with a predetermined radiation dose of gamma ray, variation in the absorbed dose of gamma ray may occur in the packaging bag. This can give rise to: medical rubber parts having low absorbed doses of gamma ray; and medical rubber parts having high absorbed doses of gamma ray. However, it may be necessary to ensure, for each medical rubber part, a minimum absorbed dose with which the medical rubber part can be sterilized. Thus, it may be necessary to irradiate the packaging bag with at least the minimum absorbed dose of gamma ray. This can give rise to medical rubber parts that absorb an excessive dose of gamma ray at the time of sterilization with gamma ray, in the packaging bag.

Japanese Laid-Open Patent Publication No. 2002-301133 discloses: a rubber composition containing an isobutylene copolymer as a main component and having a density not higher than 0.95, the rubber composition being for use in a medical rubber plug or a medical rubber product on which radiation treatment is easily performed; and a crosslinked product of the rubber composition.

Japanese Laid-Open Patent Publication (Translation of PCT Application) No. 2017-531604 discloses a method for packaging a part (1) made from an elastomer, such as a plug for a pharmaceutical agent container. The method includes: a step of packing the part (1) into a primary bag (10) made from a material substantially impermeable with air; and a step of applying an atmosphere with at least 80% of nitrogen to the inside of the primary bag (10). In the method, the primary bag (10) is put into a secondary bag (20), and the interval between the primary bag (10) and the secondary bag (20) is set to be in a vacuum state.

When a medical rubber part is sterilized by being irradiated with gamma ray, cleavage and crosslinking can simultaneously occur in a polymer that forms the medical rubber part. If an excessive dose of gamma ray is absorbed, cleavage of the main chain of the polymer that forms the medical rubber part may be promoted, whereby low-molecular-weight components may be generated. Consequently, the non-eluting performance of the medical rubber part having been sterilized with gamma ray may deteriorate.

As the medical rubber part, there is a medical rubber part that includes a body made from an elastic material and that includes an inactive resin film stacked on at least a portion of a surface of the body, from the viewpoint of enhancing non-eluting characteristics and/or slidability. However, if the medical rubber part that includes the body made from an elastic material and that includes the inactive resin film stacked on at least a portion of the surface of the body is irradiated with gamma ray, the inactive resin film may degrade. If the inactive resin film degrades, non-eluting characteristics of the medical rubber part may deteriorate. Therefore, a problem may arise in that the medical rubber part in which the inactive resin film is stacked is not suitable for being sterilized with gamma ray.

SUMMARY

A sterilization method for a medical rubber part according to one or more embodiments of the present disclosure can be a sterilization method for a medical rubber part that includes a body made from an elastic material and that includes an inactive resin film stacked on at least a portion of a surface of the body, the sterilization method including irradiating a packaging article for the medical rubber part with gamma ray, the packaging article accommodating a plurality of the medical rubber parts and having an oxygen concentration not higher than 5%.

DETAILED DESCRIPTION

Figure 1:
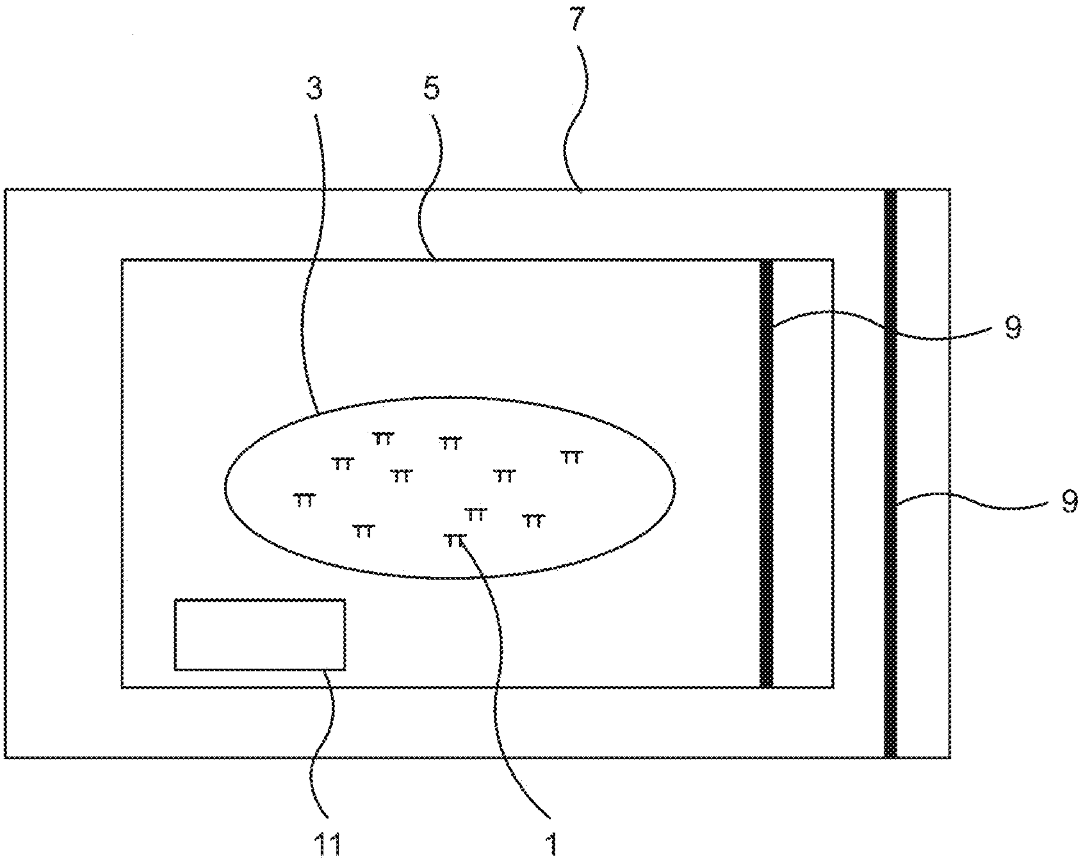
FIG. 1 is a diagram for schematically explaining an example of a packaging mode for medical rubber parts according to one or more embodiments of the present disclosure.

One or more embodiments of the present invention have been made in view of the above circumstances, and an object of the one or more embodiments of present disclosure can be to provide or implement a sterilization method for a medical rubber part that includes a body made from an elastic material and that includes an inactive resin film stacked on at least a portion of a surface of the body, with non-eluting characteristics of the medical rubber part being maintained even after sterilization with gamma ray.

One or more embodiments of the present disclosure can make it possible to provide a sterilization method for a medical rubber part that includes a body made from an elastic material and that includes an inactive resin film stacked on at least a portion of a surface of the body, with non-eluting characteristics of the medical rubber part being maintained even when the medical rubber part is sterilized with gamma ray. In addition, the inactive resin film of the medical rubber part having been sterilized with gamma ray may not have been degraded, and thus the medical rubber part can have excellent slidability and/or drug solution sealing performance.

A sterilization method for a medical rubber part according to one or more embodiments of the present disclosure can thus be a sterilization method for a medical rubber part that includes a body made from an elastic material and that includes an inactive resin film stacked on at least a portion of a surface of the body, the sterilization method including irradiating a packaging article for the medical rubber part with gamma ray, the packaging article accommodating a plurality of the medical rubber parts and having an oxygen concentration not higher than 5%.

<Sterilization Method>

Firstly, exemplary embodiments of the sterilization method according to the present disclosure will be described. Examples of the gamma ray can include gamma rays emitted from cobalt-60, cesium-137, and the like. Gamma ray emitted from cobalt-60 can be suitable.

Regarding irradiation with the gamma ray, an absorbed dose of the gamma ray by the medical rubber part can be set through an actual sterilization validation procedure. For ordinary medical devices, for instance, operation can be performed with a minimum absorbed dose being set to 15 kGy. A gamma ray radiation dose at which the absorbed doses of the gamma ray by all of the medical rubber parts in the packaging article take values not lower than 15 kGy, can vary depending on the number of the medical rubber parts in the packaging article, how the medical rubber parts are present in the packaging article, and the like. In general, irradiation can be performed in a dose that falls within a range of not lower than 1.4 times 15 kGy and not higher than 2.0 times 15 kGy. Likewise, if the minimum absorbed dose is set to 20 kGy, irradiation can be performed in a dose that falls within a range of not lower than 1.4 times 20 kGy and not higher than 2.0 times 20 kGy, and, if the minimum absorbed dose is set to 25 kGy, irradiation can be performed in a dose that falls within a range of not lower than 1.4 times 25 kGy and not higher than 2.0 times 25 kGy, as examples. The absorbed dose of the gamma ray can be ascertained through attachment of a dosemeter to an object that is to be irradiated.

The packaging article accommodating the medical rubber parts not having yet been irradiated with the gamma ray can have an oxygen concentration that is preferably not higher than 5%, more preferably lower than 5%, further preferably not higher than 3%, and particularly preferably not higher than 1%. As an example, this can be because, if the oxygen concentration in the packaging article is set to be not higher than 5%, degradation of each medical rubber part due to irradiation with the gamma ray can be suppressed.

Examples of a method for setting the oxygen concentration in the packaging article to be not higher than 5% can include: a method in which air in the packaging article is substituted with an inert gas; and a method in which an oxygen adsorber is accommodated in the packaging article.

Examples of the inert gas can include: rare gases such as helium gas, neon gas, and argon gas; nitrogen gas; and the like.

Examples of the oxygen adsorber can include AGELESS (commercially available product) which is an iron-based oxygen adsorber, and the like.

The packaging article for accommodating the medical rubber part may not be particularly limited, for instance, as long as the packaging article can be irradiated with the gamma ray. Examples of the form of the packaging article can include the forms of a bag, a box, and the like. Examples of the packaging bag can include packaging bags formed of aluminum or a thermoplastic resin film made from polyethylene, polyamide, or polyester. The packaging bag can be preferably one that can be sealed. The packaging box may not be particularly limited, and examples of the packaging box can include a box made from paper, a box made from cardboard, and the like.

Examples of the packaging article can include: a packaging article having gas permeability; and a packaging article having non-gas permeability (gas sealability). It may also be preferable to use these packaging articles in combination.

Irradiation of the medical rubber part with the gamma ray may be performed on, for example, a packaging article (for example, a cardboard box) further accommodating a plurality of primary packaging articles (for example, packaging bags) accommodating a plurality of the medical rubber parts.

FIG. 1 is a diagram for schematically explaining an example of a packaging mode for irradiation with the gamma ray according to one or more embodiments of the present disclosure. In the mode shown in FIG. 1, a primary packaging article 3 accommodating a plurality of medical rubber ¯parts 1 can be further accommodated in a secondary static charge prevention packaging article 5 and a tertiary static charge prevention packaging article 7. As the primary packaging article 3, a packaging article having gas permeability may be preferable. As the secondary static charge prevention packaging article 5 and the tertiary static charge prevention packaging article 7, packaging articles capable of sealing gas therein may be preferable. Each of the secondary static charge prevention packaging article 5 and the tertiary static charge prevention packaging article 7 may preferably be sealed with a heat seal 9. In the case of using an oxygen adsorber 11, the oxygen adsorber 11 can be preferably disposed between the primary packaging article 3 and the secondary packaging article 5 such that the oxygen adsorber 11 does not come into direct contact with the medical rubber parts 1. By disposing the oxygen adsorber 11 in the secondary packaging article 5, the oxygen concentration in each of the secondary packaging article 5 and the primary packaging article 3 can be set to be not higher than 5%, for instance. Irradiation with the gamma ray can be performed with a plurality of the tertiary static charge prevention packaging articles 7 being accommodated in a quaternary packaging article (for example, a cardboard box).

Figure 2:
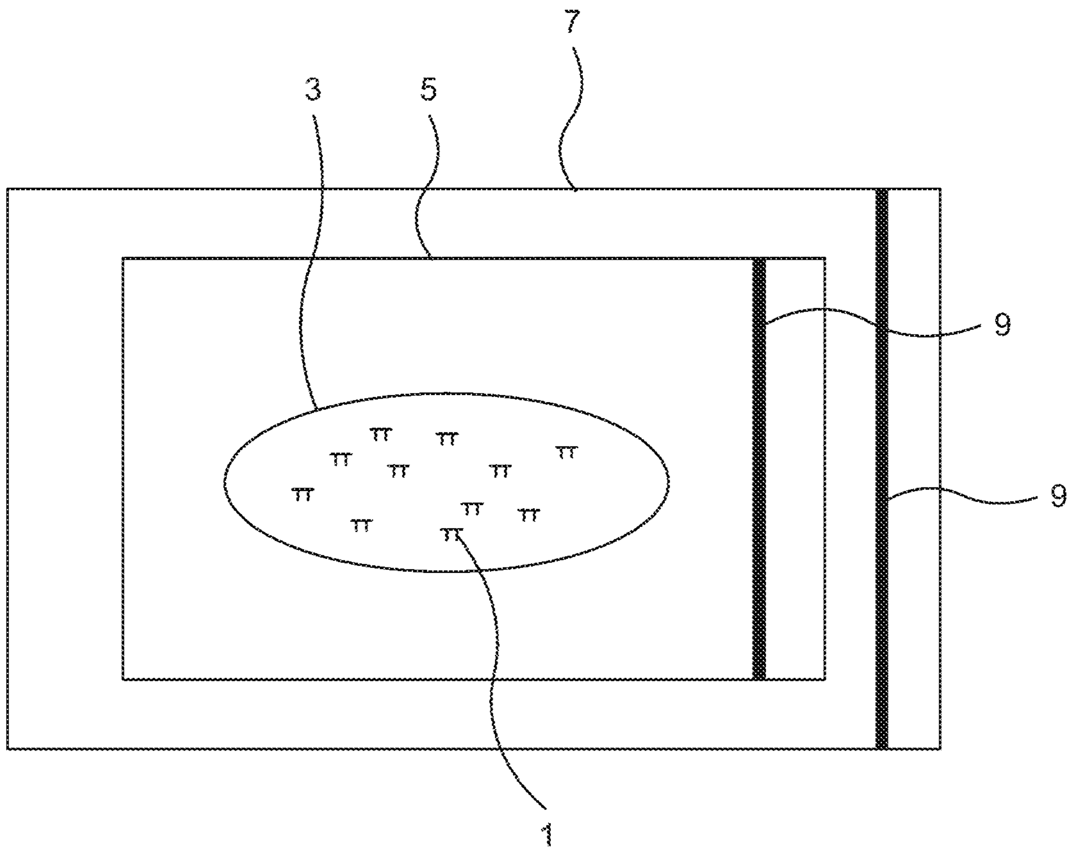
FIG. 2 is a diagram for schematically explaining another example of the packaging mode for the medical rubber parts according to one or more embodiments of the present disclosure.

FIG. 2 is a diagram for schematically explaining another example of the packaging mode for irradiation with the gamma ray. In the mode shown in FIG. 2, the primary packaging article 3 accommodating the plurality of medical rubber parts 1 may be further accommodated in the secondary static charge prevention packaging article 5 and the tertiary static charge prevention packaging article 7. Each of the secondary static charge prevention packaging article 5 and the tertiary static charge prevention packaging article 7 may be preferably sealed with the heat seal 9. As the primary packaging article 3, a packaging article having gas permeability may be preferable. As the secondary static charge prevention packaging article 5 and the tertiary static charge prevention packaging article 7, packaging articles capable of sealing gas therein can be preferable. The secondary packaging article 5 accommodating the primary packaging article 3 can be filled with an inert gas. The filling with the inert gas can make it possible to set the oxygen concentration in each of the secondary packaging article 5 and the primary packaging article 3 to be not higher than 5%, as an example. Irradiation with the gamma ray can be performed with a plurality of the tertiary static charge prevention packaging articles 7 being accommodated in a quaternary packaging article (for example, a cardboard box).

At the time of irradiation with the gamma ray, irradiation with the gamma ray can be preferably performed in a state where the packaging article accommodating the plurality of medical rubber parts is accommodated in, for example, an accommodation container made from an aluminum alloy.

<Medical Rubber Part>

Next, the medical rubber part to which one or more embodiments of the present disclosure can be applied will be described. The medical rubber part to which one or more embodiments of the present disclosure can be applied can include: a body made from an elastic material; and an inactive resin film stacked on at least a portion of a surface of the body.

<Elastic Material Forming Body of Medical Rubber Part>

The elastic material may not be particularly limited, for instance, as long as the elastic material is, for example, an object characterized by being deformed upon application of a force and reassuming the original shape upon elimination of the force.

From this viewpoint, a compression set of the elastic material measured at 70° C. 22 hours later according to the measurement method described in JIS K 6262: 2013, may be preferably not higher than 20%, more preferably not higher than 15%, and further preferably not higher than 10%. The lower limit of the compression set of the elastic material may not be particularly limited.

The elastic material can have a rubber hardness indicated as a type A durometer hardness (Shore A hardness) measured according to the measurement method described in the Japanese Industrial Standard JIS K 6253-3: 2012 "Rubber, vulcanized or thermoplastic—Determination of hardness—Part 3: Durometer method." The rubber hardness can be preferably not lower than 30, more preferably not lower than 35, and further preferably not lower than 40. Meanwhile, the rubber hardness can be preferably not higher than 70, more preferably not higher than 65, and further preferably not higher than 60.

Examples of the material composing the elastic material can include a rubber, a thermoplastic elastomer, and the like.

Examples of the thermoplastic elastomer include polyurethane-based elastomers, polyester-based elastomers, polyamide-based elastomers, olefin-based elastomers, styrene-based elastomers, and the like.

Examples of the rubber composing the elastic material can include butyl-based rubbers, isoprene rubber, butadiene rubber, styrene-butadiene rubber, natural rubber, chloroprene rubber, nitrile-based rubbers such as acrylonitrile-butadiene rubber, hydrogenated nitrile-based rubbers, norbornene rubber, ethylene-propylene rubber, ethylene-propylene-diene rubber, acrylic rubber, ethylene-acrylate rubber, fluororubber, chlorosulfonated polyethylene rubber, epichlorohydrin rubber, silicone rubber, urethane rubber, polysulfide rubber, phosphazene rubber, 1,2-polybutadiene, and the like. Among these rubbers, a butyl-based rubber may be preferable and a halogenated isobutylene-isoprene rubber may be more preferable as the rubber composing the elastic material.

These materials composing the elastic material may be used singly, or a plurality of these components may be blended to be used.

The elastic material that forms the body of the medical rubber part can be preferably a cured product of a medical rubber composition containing a (a) base polymer containing a halogenated isobutylene-isoprene rubber. Hereinafter, raw materials that may be contained in the medical rubber composition will be described.

First, the (a) base polymer containing a halogenated isobutylene-isoprene rubber will be described. Examples of the halogenated isobutylene-isoprene rubber can include: chlorinated isobutylene-isoprene rubber; brominated isobutylene-isoprene rubber; a bromide of a copolymer rubber of isobutylene and p-methylstyrene (brominated isobutylene-para-methylstyrene copolymer rubber); and the like.

As the halogenated isobutylene-isoprene rubber, chlorinated isobutylene-isoprene rubber or brominated isobutylene-isoprene rubber may be preferable. The chlorinated isobutylene-isoprene rubber or the brominated isobutylene-isoprene rubber can be obtained by, for example, causing a reaction in which: chlorine or bromine is added to an isoprene structural moiety (specifically, a double bond and/or a carbon atom adjacent to the double bond) in an isobutylene-isoprene rubber; or the isoprene structural moiety is substituted with chlorine or bromine. The isobutylene-isoprene rubber can be a copolymer obtained by polymerizing isobutylene and a small amount of isoprene.

The halogen content of the halogenated isobutylene-isoprene rubber can be preferably not lower than 0.5% by mass, more preferably not lower than 1% by mass, and further preferably not lower than 1.5% by mass. Meanwhile, the halogen content can be preferably not higher than 5% by mass, more preferably not higher than 4% by mass, and further preferably not higher than 3% by mass.

Specific examples of the chlorinated isobutylene-isoprene rubber can include at least one of: CHLOROBUTYL 1066 [stabilizer: NS, halogen content: 1.26%, Mooney viscosity: 38 $ML_{1+8}$ (125° C.), specific gravity: 0.92] manufactured by JAPAN BUTYL Co., Ltd.; LANXESS X_BUTYL CB1240 manufactured by LANXESS; and/or the like.

Specific examples of the brominated isobutylene-isoprene rubber include at least one of: BROMOBUTYL 2255 [stabilizer: NS, halogen content: 2.0%, Mooney viscosity: 46 $ML_{1+8}$ (125° C.), specific gravity: 0.93] manufactured by JAPAN BUTYL Co., Ltd.; LANXESS X_BUTYL BBX2 manufactured by LANXESS; and/or the like.

The (a) base polymer may contain a rubber component other than the halogenated isobutylene-isoprene rubber.

Examples of the other rubber component can include butyl-based rubbers, isoprene rubber, butadiene rubber, styrene-butadiene rubber, natural rubber, chloroprene rubber, nitrile-based rubbers such as acrylonitrile-butadiene rubber, hydrogenated nitrile-based rubbers, norbornene rubber, ethylene-propylene rubber, ethylene-propylene-diene rubber, acrylic rubber, ethylene-acrylate rubber, fluororubber, chlorosulfonated polyethylene rubber, epichlorohydrin rubber, silicone rubber, urethane rubber, polysulfide rubber, phosphazene rubber, 1,2-polybutadiene, and the like. These rubber components may be used singly, or two or more of these rubber components may be used in combination.

In the case of using the other rubber component, the proportion of the halogenated isobutylene-isoprene rubber contained in the (a) base polymer can be preferably not lower than 90% by mass, more preferably not lower than 95% by mass, and further preferably not lower than 98% by mass. A mode in which the (a) base polymer contains only the halogenated isobutylene-isoprene rubber may also be preferable.

The medical rubber composition according to one or more embodiments of the present disclosure preferably can comprise or contain a (b) crosslinking agent. The (b) crosslinking agent may be blended to cause crosslinking in the halogenated isobutylene-isoprene rubber component contained in the (a) base polymer. The (b) crosslinking agent may not be particularly limited as long as the crosslinking agent can cause crosslinking in the halogenated isobutylene-isoprene rubber. Examples of the (b) crosslinking agent can include a sulfur, a metal oxide, a resin crosslinking agent, an organic peroxide, a triazine derivative, and the like. These crosslinking agents may be used singly, or two or more of these crosslinking agents may be used in combination.

Examples of the sulfur used as the crosslinking agent can include powdered sulfur, finely powdered sulfur, precipitated sulfur, colloidal sulfur, sulfur chloride, and the like.

Examples of the metal oxide used as the crosslinking agent can include magnesium oxide, calcium oxide, zinc oxide, copper oxide, and the like.

Examples of the resin crosslinking agent can include alkylphenol-formaldehyde resins such as an alkylphenol-formaldehyde resin, a thermally reactive phenol resin, a phenol dialcohol-based resin, a bisphenol resin, and a thermally reactive bromomethyl alkylated phenol resin.

Specific examples of the organic peroxide can include dialkyl peroxides, peroxyesters, peroxyketals, hydroperoxides, and the like. Examples of the dialkyl peroxides can include di(2-t-butylperoxyisopropyl)benzene, dicumyl peroxide, 2,5-dimethyl-2,5-di(t-butylperoxy)hexane, t-butylcumyl peroxide, di-t-hexyl peroxide, di-t-butyl peroxide, 2,5-dimethyl-2,5-di(t-butylperoxy)hexyne-3, and the like. Examples of the peroxyesters include t-butylperoxymaleate, t-butylperoxy-3,3,5-trimethylcy clohexanoate, t-butylperoxylaurate, t-butylperoxyisopropyl monocarbonate, t-hexylperoxybenzoate, 2,5-dimethyl-2,5-di(benzoylperoxy)hexane, t-butylperoxyacetate, t-butylperoxybenzoate, and the like. Examples of the peroxyketals include 1,1-di(t-hexylperoxy)-3,3,5-trimethylcyclohexane, 1,1-di(t-hexylperoxy)cyclohexane, 1,1-di(t-butylperoxy)-2-methylcyclohexane, 1,1-di(t-butylperoxy)cyclohexane, 2,2-di(t-butylperoxy)butane, n-butyl-4,4-di(t-butylperoxy)valerate, 2,2-di(4,4-di(t-butylperoxy)cyclohexyl)propane, and the like. Examples of the hydroperoxides can include p-menthane hydroperoxide, diisopropylbenzene hydroperoxide, and the like. These organic peroxides may be used singly, or two or more of these organic peroxides may be used in combination.

The medical rubber composition according to one or more embodiments of the present disclosure may contain or comprise a triazine derivative as the (b) crosslinking agent.

Examples of the triazine derivative can include a compound represented by a general formula (1).

[Chem. 1]

(1)

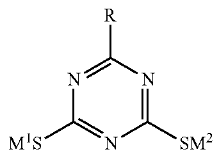

[in the formula, R represents —SH, —$OR^1$, —$SR^2$, —$NHR^3$, or —$NR^4R^5$ ($R^1$, $R^2$, $R^3$, $R^4$, and $R^5$ each represent an alkyl group, an alkenyl group, an aryl group, an aralkyl group, an alkylaryl group, or a cycloalkyl group. $R^4$ and $R^5$ may be identical to each other or different from each other). $M^1$ and $M^2$ each represent H, Na, Li, K, ½Mg, ½Ba, ½Ca, an aliphatic primary, secondary, or tertiary amine, a quaternary ammonium salt, or a phosphonium salt. $M^1$ and $M^2$ may be identical to each other or different from each other.]

In the general formula (1), examples of the alkyl group can include alkyl groups having 1 to 12 carbon atoms, such as a methyl group, an ethyl group, an n-propyl group, an isopropyl group, an n-butyl group, an isobutyl group, a tert-butyl group, an n-pentyl group, an isopentyl group, a tert-pentyl group, an n-hexyl group, a 1,1-dimethylpropyl group, an octyl group, an isooctyl group, a 2-ethylhexyl group, a decyl group, and a dodecyl group. Examples of the alkenyl group can include alkenyl groups having 1 to 12 carbon atoms, such as a vinyl group, an allyl group, a 1-propenyl group, an isopropenyl group, a 2-butenyl group, a 1,3-butadienyl group, and a 2-pentenyl group. Examples of the aryl group can include monocyclic aromatic hydrocarbon groups and condensed polycyclic aromatic hydrocarbon groups, and examples thereof include: aryl groups having 6 to 14 carbon atoms, such as a phenyl group, a naphthyl group, an anthryl group, a phenanthryl group, and an acenaphthylenyl group; and the like. Examples of the aralkyl group can include aralkyl groups having 7 to 19 carbon atoms, such as a benzyl group, a phenethyl group, a diphenylmethyl group, a 1-naphthylmethyl group, a 2-naphthylmethyl group, a 2,2-diphenylethyl group, a 3-phenylpropyl group, a 4-phenylbutyl group, a 5-phenylpentyl group, a 2-biphenylylmethyl group, a 3-biphenylylmethyl group, and a 4-biphenylylmethyl group. Examples of the alkylaryl group include alkylaryl groups having 7 to 19 carbon atoms, such as a tolyl group, a xylyl group, and an octylphenyl group. Examples of the cycloalkyl group can include: cycloalkyl groups having 3 to 9 carbon atoms, such as a cyclopropyl group, a cyclobutyl group, a cyclopentyl group, a cyclohexyl group, a cycloheptyl group, a cyclooctyl group, and a cyclononyl group; and the like.

Specific examples of the triazine derivative represented by the general formula (1) can include 2,4,6-trimercapto-s-triazine, 2-methylamino-4,6-dimercapto-s-triazine, 2-(n-butylamino)-4,6-dimercapto-s-triazine, 2-octylamino-4,6-dimercapto-s-triazine, 2-propylamino-4,6-dimercapto-s-triazine, 2-diallylamino-4,6-dimercapto-s-triazine, 2-dimethylamino-4,6-dimercapto-s-triazine, 2-dibutylamino-4,6-dimercapto-s-triazine, 2-di(iso-butylamino)-4,6-dimercapto-s-triazine, 2-dipropylamino-4,6-dimercapto-s-triazine, 2-di(2-ethylhexyl)amino-4,6-dimercapto-s-triazine, 2-dioleylamino-4,6-dimercapto-s-triazine, 2-laurylamino-4,6-dimercapto-s-triazine, 2-anilino-4,6-dimercapto-s-triazine, and sodium salts and disodium salts of these triazine derivatives.

Among these triazine derivatives, 2,4,6-trimercapto-s-triazine, 2-dialkylamino-4,6-dimercapto-s-triazine, and 2-anilino-4,6-dimercapto-s-triazine are preferable, and 2-dibutylamino-4,6-dimercapto-s-triazine may be particularly preferable since 2-dibutylamino-4,6-dimercapto-s-triazine may be relatively easy to obtain.

Other examples of the triazine derivative can include one or more of 6-[bis(2-ethylhexyl)amino]-1,3,5-triazine-2,4-dithiol, 6-diisobutylamino-1,3,5-triazine-2,4-dithiol, 6-dibutylamino-1,3,5-triazine-2,4-dithiol, 6-dibutylamino-1,3,5-triazine-2,4-dithiol monosodium, 6-anilino-1,3,5-triazine-2,4-dithiol, 1,3,5-triazine-2,4,6-trithiol, and the like.

In the medical rubber composition according to one or more embodiments of the present disclosure, these triazine derivatives may be used singly, or two or more of these triazine derivatives may be used in combination.

In the medical rubber composition according to one or more embodiments of the present disclosure, the amount of the (b) crosslinking agent contained per 100 parts by mass of the (a) base polymer component can be preferably not smaller than 0.1 parts by mass, more preferably not smaller than 0.3 parts by mass, and further preferably not smaller than 0.5 parts by mass. Meanwhile, the amount can be preferably not larger than 2.0 parts by mass, more preferably not larger than 1.4 parts by mass, and further preferably not larger than 1.2 parts by mass. This can be, for instance, because, if the amount of the (b) crosslinking agent contained falls within the aforementioned range, a rubber having favorable rubber physical properties (hardness, tensile properties, Cset) and good eluting performance and processability (less susceptibility to scorching) can be obtained.

The medical rubber composition according to one or more embodiments of the present disclosure can preferably contain no vulcanization accelerator. This can be, for instance, because a vulcanization accelerator may remain in a rubber product obtained as a final product and could elute into a drug solution inside a syringe or a vial. Examples of the vulcanization accelerator can include guanidine-based accelerators (e.g., diphenylguanidine), thiuram-based accelerators (e.g., tetramethylthiuram disulfide and tetramethylthiuram monosulfide), dithiocarbamate-based accelerators (e.g., zinc dimethyldithiocarbamate), thiazole-based accelerators (e.g., 2-mercaptobenzothiazole and dibenzothiazyl disulfide), and sulfenamide-based accelerators (N-cyclohexyl-2-benzothiazole sulfenamide and N-t-butyl-2-benzothiazole sulfenamide).

The medical rubber composition according to one or more embodiments of the present disclosure may contain or comprise a hydrotalcite. The hydrotalcite can function as an anti-scorching agent upon crosslinking in the halogenated isobutylene-isoprene rubber and/or also can have a function of preventing increase in compression set in the medical rubber part. Further, the hydrotalcite can also function as an acid acceptor for absorbing chlorine-based gas and bromine-based gas, which may have been generated upon crosslinking in the halogenated isobutylene-isoprene rubber, and/or preventing occurrence of, for example, crosslinking inhibition due to these gases. The aforementioned magnesium oxide can also function as an acid acceptor.

Examples of the hydrotalcite can include one or more of Mg—Al-based hydrotalcites such as $Mg_{4.5}Al_2(OH)_{13}CO_{3.3}\cdot 5H_2O$, $Mg_{4.5}Al_2(OH)_{13}CO_3$, $Mg_4Al_2(OH)_{12}CO_3\cdot 3.5H_2O$, $Mg_6Al_2(OH)_{16}CO_3\cdot 4H_2O$, $Mg_5Al_2(OH)_{14}CO_3\cdot 4H_2O$, and $Mg_3Al_2(OH)_{10}CO_3\cdot 1.7H_2O$, and the like.

Specific examples of the hydrotalcite can include DHT-4A (registered trademark)-2 manufactured by Kyowa Chemical Industry Co., Ltd., and the like.

In the case where the hydrotalcite is used as an acid acceptor in the medical rubber composition, the hydrotalcite can be preferably used in combination with MgO. In this case, the blending amount of the hydrotalcite can be preferably considered in terms of the total amount of the acid acceptors (hydrotalcite and MgO). The total amount of the acid acceptors (hydrotalcite and MgO) contained per 100 parts by mass of the (a) base polymer component can be preferably not smaller than 0.5 parts by mass and more preferably not smaller than 1 part by mass. Meanwhile, the total amount can be preferably not larger than 15 parts by mass and more preferably not larger than 10 parts by mass. This can be, for instance, because, if the total amount of the acid acceptors (hydrotalcite and MgO) falls within the aforementioned range, generation of rust on a mold or the like can be suppressed, and defects that raw materials themselves turn into an unwanted object in the form of a white spot can be reduced.

The medical rubber composition according to one or more embodiments of the present disclosure may contain or comprise a co-crosslinking agent. The co-crosslinking agent can be preferably a polyfunctional (meth)acrylate compound. The polyfunctional (meth)acrylate compound can be more preferably a difunctional or higher-functional (meth)acrylate-based compound and further preferably a trifunctional or higher-functional (meth)acrylate-based compound. Meanwhile, the polyfunctional (meth)acrylate compound can be preferably an octafunctional or lower-functional (meth)acrylate-based compound and more preferably a hexafunctional or lower-functional (meth)acrylate-based compound. Examples of the difunctional or higher-functional (meth)acrylate compound can include a compound having at least two acryloyl groups and/or methacryloyl groups. The term "(meth)acrylate" can mean "acrylate" and/or "methacrylate."

Examples of the difunctional or higher-functional (meth)acrylate-based compound can include di(meth)acrylate of polyethylene glycol, 1,4-butanediol di(meth)acrylate, 1,6-hexanediol di(meth)acrylate, 1,9-nonanediol di(meth)acrylate, trimethylolpropane tri(meth)acrylate, trimethylolethane tri(meth)acrylate, pentaerythritol tri(meth)acrylate, pentaerythritol tetra(meth)acrylate, glycerin tri(meth)acrylate, dipentaerythritol tri(meth)acrylate, dipentaerythritol tetra (meth)acrylate, dipentaerythritol penta(meth)acrylate, dipentaerythritol hexa(meth)acrylate, tripentaerythritol tetra (meth)acrylate, tripentaerythritol penta(meth)acrylate, tripentaerythritol hexa(meth)acrylate, tripentaerythritol hepta (meth)acrylate, and the like. These co-crosslinking agents may be used singly, or two or more of these co-crosslinking agents may be used in combination.

In the medical rubber composition according to one or more embodiments of the present disclosure, a filler may be blended. Examples of the filler can include inorganic fillers such as silica, clay, and talc. The filler can be further preferably clay or talc. The filler can have a function of adjusting the rubber hardness of the medical rubber part and/or a function as an extender for reducing manufacturing cost for the medical rubber part.

Examples of the clay can include calcined clay and kaolin clay. Specific examples of the clay can include SILLITIN (registered trademark) Z manufactured by Hoffmann Mineral GmbH, SATINTONE (registered trademark) W manufactured by Engelhard Corporation, NN Kaolin Clay manufactured by Tsuchiya Kaolin Industry Co., Ltd., PoleStar200R manufactured by Imerys Specialties Japan Co., Ltd., and the like.

Specific examples of the talc can include High toron A manufactured by Takehara Kagaku Kogyo Co., Ltd., MICRO ACE (registered trademark) K-1 manufactured by Nippon Talc Co., Ltd., MISTRON (registered trademark) Vapor manufactured by Imerys Specialties Japan Co., Ltd., and the like.

In the medical rubber composition according to one or more embodiments of the present disclosure, a colorant such as titanium oxide or carbon black, polyethylene glycol as a processing aid or as a crosslinking activator, a plasticizer (for example, paraffin oil), and the like may further be blended in appropriate proportions.

<Inactive Resin Film>

The medical rubber part to which one or more embodiments of the present disclosure can be applied can include: a body made from an elastic material; and an inactive resin film stacked on at least a portion of a surface of the body. The inactive resin film can prevent any of the components composing the elastic material from eluting to a pharmaceutical agent. In addition, the inactive resin film can impart, for example, slidability and/or drug solution sealing performance to the medical rubber part.

The inactive resin film may only have to be stacked on at least a portion of the surface of the body, made from the elastic material, of the medical rubber part. The inactive resin film can be preferably stacked as appropriate according to the form of the medical rubber part.

The resin that forms the inactive resin film may not be particularly limited. However, from the viewpoint of obtaining favorable chemical resistance, the resin may be preferably an olefin-based resin or at least one type of fluorine resin selected from the group consisting of tetrafluoroethylene-ethylene copolymer (ETFE), polytetrafluoroethylene (PTFE), and/or poly chlorotetrafluoroethylene (PCTFE).

The tetrafluoroethylene-ethylene copolymer (ETFE) can be obtained by copolymerizing ethylene and tetrafluoroethylene in a molar ratio of 30/70 to 70/30, for instance, and examples of the ETFE can include a modified ETFE obtained by further copolymerizing another component for the purpose of modification. Examples of the other component can include fluorine-containing olefins and hydrocarbon-based olefins. Specific examples of the other component can include: α-olefins such as propylene and butene; fluorine-containing olefins such as hexafluoropropylene, vinylidene fluoride, perfluorobutylethylene, and trifluorochloroethylene; vinyl ethers such as ethylene vinyl ether, perfluoromethyl vinyl ether, and perfluoropropyl vinyl ether; fluorine-containing acrylates; and the like. About 2 to 10% by mole of the other component can be copolymerized to modify the ETFE, according to one or more embodiments of the present disclosure.

As the modified ETFE, an ETFE having a functional group for imparting adhesiveness can be suitably used. Examples of the functional group can include a carboxyl group, a carboxylic anhydride group, an epoxy group, a hydroxy group, an isocyanate group, an ester group, an amide group, an aldehyde group, an amino group, a cyano group, a carbon-carbon double bond, a sulfonic acid group, an ether group, and the like. Examples of commercially available modified ETFEs can include Fluon AH-2000 manufactured by AGC Inc., and the like.

Examples of the olefin-based resin can include: polyethylene-based resins such as polyethylene, ethylene-propylene copolymers, ethylene-propylene-non-conjugated diene copolymers, ethylene-butene copolymers, ethylene-hexene copolymers, ethylene-octene copolymers, ethylene-vinyl acetate copolymers, ethylene-vinyl alcohol copolymers, ethylene-ethyl acrylate copolymers, and chlorinated polyethylene; polypropylene-based resins such as polypropylene, propylene-ethylene random copolymers, propylene-ethylene block copolymers, and chlorinated polypropylene; copolymers of polybutene, polyisobutylene, polymethylpentene, and cyclic olefins; and the like. Among these olefin-based resins, polyethylene (especially, ultrahigh-molecular-weight polyethylene (UHMWPE)) may be preferable. The olefin-based resin may contain or comprise fluorine.

The thickness of the inactive resin film may be adjusted as appropriate according to the shape and the size of the medical rubber part. According to one or more embodiments of the present disclosure, the thickness can be preferably not smaller than 10 μm, more preferably not smaller than 20 μm, and further preferably not smaller than 30 μm. Meanwhile, the thickness can be preferably not larger than 150 μm, more preferably not larger than 130 μm, and further preferably not larger than 110 μm. The reason(s) can be as follows. That is, if the thickness of the inactive resin film falls within the aforementioned range, the film may not be torn during molding of a product, and the film on the surface of the post-molding product may not experience wrinkle, floating defect, and/or the like, whereby both moldability and/or product characteristics can be achieved.

The inactive resin film can have an arithmetic average roughness Ra. In a case where the inactive resin film is a cast film or an extruded film, this roughness can be 0.01 to 0.03 μm, whereas, in a case where the inactive resin film is a skived film, this roughness can be 0.10 μm, and in this case as well, a medical rubber part having excellent liquid adhesiveness and airtightness can be obtained by setting the surface roughness of a mold to be not larger than 0.03 μm. The lower limit of Ra of the inactive resin film itself may not be particularly limited.

The inactive resin film can be preferably subjected to treatment for improving the adhesiveness to rubber or the like. Examples of the treatment for improving the adhesiveness can include chemical treatment, treatment for roughening the surface of the film, and a combination thereof. Specific examples of the treatment for improving the adhesiveness can include sodium treatment, glow discharge treatment, plasma treatment (discharge treatment) under atmospheric pressure or under a vacuum, excimer laser treatment (discharge treatment), and ion beam treatment.

Regarding the medical rubber part to which one or more embodiments of the present disclosure can be applied, for example, press-molding can be performed in a state where the inactive resin film is superposed on a sheet made from the elastic material, whereby a medical rubber part in which the body made from the elastic material and the inactive resin film have been integrated can be obtained.

Specifically, the (a) base polymer containing or comprising the halogenated isobutylene-isoprene rubber, the (b) crosslinking agent, and other blending materials to be added as necessary or desired can be kneaded to obtain the medical rubber composition according to one or more embodiments of the present disclosure. The kneading can be performed by using, for example, an open roll, a sealed-type kneader, or the like. The kneaded product can be preferably molded in the shape of a ribbon, the shape of a sheet, the shape of a pellet, or the like, and can be more preferably molded in the shape of a sheet.

The inactive resin film can be stacked on the obtained rubber in the form of a sheet, and press-molding can be performed, whereby a medical rubber part in which the body made from the elastic material and the inactive resin film have been integrated can be obtained.

A crosslinking reaction in the medical rubber composition can progress during the pressing. The temperature in the molding can be, for example, preferably not lower than 130° C. and more preferably not lower than 140° C. Meanwhile, the temperature can be preferably not higher than 200° C. and more preferably not higher than 190° C. The time for the molding can be preferably not shorter than 2 minutes and more preferably not shorter than 3 minutes. Meanwhile, the time can be preferably not longer than 60 minutes and more preferably not longer than 30 minutes. The pressure for the molding can be preferably not lower than 0.1 MPa and more preferably not lower than 0.2 MPa. Meanwhile, the pressure can be preferably not higher than 10 MPa and more preferably not higher than 8 MPa.

Unnecessary portions may be cut off and removed from the molded product after the press-molding, such that the molded product has a predetermined shape. The obtained molded product can be washed, dried, and packaged to manufacture the medical rubber part.

Some examples of the medical rubber part to which one or more embodiments of the present disclosure can be applied can include: rubber plugs and sealing members of containers for various medical preparations such as a liquid preparation, a powder preparation, and a freeze-dried preparation; slidable parts and sealing parts such as rubber plugs for vacuum blood collection tubes, and plunger stoppers and nozzle caps for pre-Tillable syringes; and the like. Hereinafter, specific examples of the medical rubber part to which one or more embodiments of the present disclosure can be applied will be described.

<Plunger Stopper>

Figure 3:
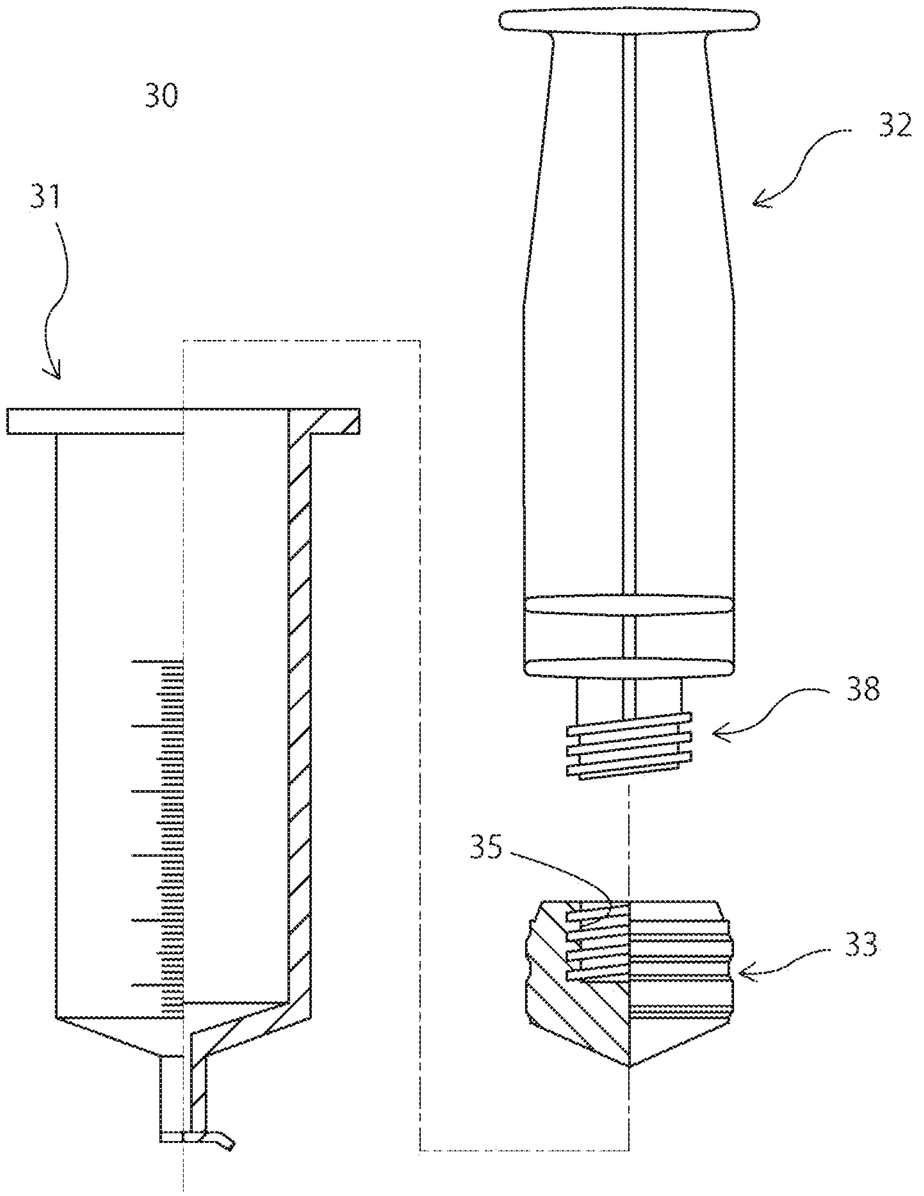
FIG. 3 is a diagram for schematically explaining an example of each of the medical rubber parts according to one or more embodiments of the present disclosure.

FIG. 3 is an exploded view of a medical injector for which the medical rubber part according to according to one or more embodiments of the present disclosure can be used, i.e., an injector that is a so-called pre-fillable syringe 30. In FIG. 3, half of each of a syringe barrel 31 and a plunger stopper 33 is shown as a cross section. The pre-Tillable syringe 30 can include or consist of: the syringe barrel 31 having a cylindrical shape; a plunger 32 combined with the syringe barrel 31 and movable in a reciprocating manner in the syringe barrel 31; and the plunger stopper 33 attached to a front end of the plunger 32. The inactive resin film, which can be to enhance slidability, can be stacked on the surface of the plunger stopper 33.

According to one or more embodiments of the present disclosure, the plunger 32 can be formed as, for example, a sheet piece that is made of a resin and that has a cross section with the shape of a cross. A front end portion of the plunger 32 can be provided with a head portion 38 to which the plunger stopper 33 is attached. The head portion 38 may be integrated with the plunger 32, can be made of a resin, and can have been processed to have the shape of an external thread. The plunger stopper 33 can have a substantially columnar shape with a short length, and a front end surface of the plunger stopper 33 can have the shape of a mountain with an obtuse angle such that an axial center portion of the front end surface protrudes, for example. An engaging recess 35 having the shape of an internal thread can be carved in an axial direction from a rear end surface of the plunger stopper 33. The head portion 38 of the plunger 32 can be screwed into the engaging recess 35 of the plunger stopper 33, whereby the plunger stopper 33 is attached to the front end of the plunger 32.

Figure 4:
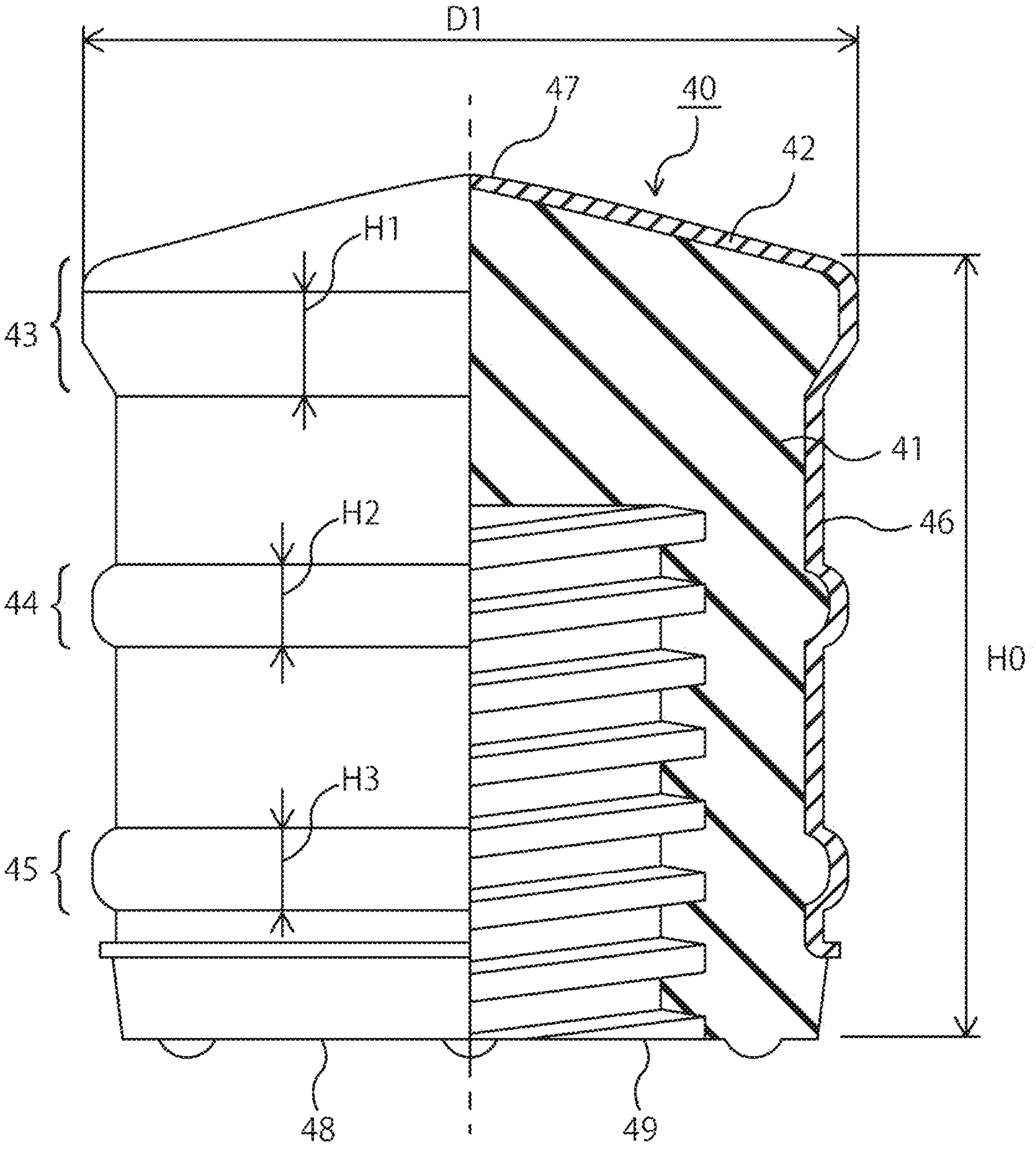
FIG. 4 is a diagram for schematically explaining an example of the medical rubber part according to one or more embodiments of the present disclosure.

FIG. 4 is a half cross-sectional front view of an example of the plunger stopper. A plunger stopper 40 can include or consist of: a body 41 made from the elastic material; and an inactive resin film 42 stacked on a surface of the body. The plunger stopper 40 can have a short columnar shape and can have a plurality of annular ribs 43, 44, and 45 on an outer circumferential surface 46 of the columnar shape. The annular ribs can be brought into sliding contact with an inner circumferential surface of the syringe barrel. The plurality of annular ribs can be arrayed in the axial direction from a front end surface 47 toward a rear end surface 48 of the plunger stopper. The number of the annular ribs may not be particularly limited as long as the number is not smaller than 1, for instance. However, the number can be preferably not smaller than 2 and more preferably not smaller than 3. Meanwhile, the number can be preferably not larger than 6, more preferably not larger than 5, and further preferably not larger than 4.

The plunger stopper 40 in FIG. 4 can have a first annular rib 43, a second annular rib 44, and a third annular rib 45 from the front end side. The first annular rib 43 at the front end can have a compression rate in a radial direction. The compression rate can be preferably not lower than 1%, more preferably not lower than 2%, and further preferably not lower than 3%. Meanwhile, the compression rate can be preferably not higher than 10%, more preferably not higher than 9%, and further preferably not higher than 8%. The compression rate can be calculated according to the following expression on the basis of an outer diameter D1 of the annular rib in an uncompressed state and an inner diameter R of the syringe barrel.

$$\text{Compression rate }(\%)=100\times(D1-R)/D1$$

A straight length H1 (the length in the axial direction) of a sliding contact portion of the annular rib 43 at the front end can be preferably not smaller than 1%, more preferably not smaller than of 3%, and further preferably not smaller than 6% of a straight length (the length in the axial direction of the outer circumferential surface) Ho of the outer circumferential surface having the columnar shape. Meanwhile, the straight length H1 can be preferably not larger than 25%, more preferably not larger than 20%, and further preferably not larger than 15% of the straight length Ho.

A straight length H2 (the length in the axial direction) of a sliding contact portion of the second annular rib 44 and a straight length H3 (the length in the axial direction) of a sliding contact portion of the third annular rib 45 can each be preferably not smaller than 1%, more preferably not smaller than 2%, and further preferably not smaller than 3% of the straight length Ho (the length in the axial direction of the outer circumferential surface) of the outer circumferential surface of the columnar shape. Meanwhile, the straight lengths H2 and H3 can each be preferably not larger than 15%, more preferably not larger than 14%, and further preferably not larger than 13% of the straight length Ho.

In the mode shown in FIG. 4, the inactive resin film 42 can be provided substantially on the entire surface (the front end surface 47 and the outer circumferential surface 46) of the body of the plunger stopper. However, the inactive resin film 42 may only have to be provided on at least a portion of the body 41 made from the elastic material. For example, the inactive resin film 42 may be stacked on only the front end surface 47 which has the shape of a mountain and which is brought into contact with a drug solution when the plunger stopper is inserted into the syringe. As the inactive resin film 42, a polytetrafluoroethylene film may be preferable.

It may also be preferable that the first annular rib 43 at the front end has, in the sliding contact portion thereof, one or more annular grooves that are formed through laser machining and that extend in a circumferential direction.

The depth of each of the annular grooves can be preferably not smaller than 2 μm, more preferably not smaller than 3 μm, and further preferably not smaller than 5 μm. Meanwhile, the depth can be preferably not larger than 100 μm, more preferably not larger than 80 μm, and further preferably not larger than 50 μm.

The width of the annular groove can be preferably not smaller than 10 μm, more preferably not smaller than 20 μm, and further preferably not smaller than 30 μm. Meanwhile, the width can be preferably not larger than 200 μm, more preferably not larger than 170 μm, and further preferably not larger than 150 μm.

The plunger stopper may sometimes be called a stopper or a gasket.

<Rubber Plug>

Figure 5A:
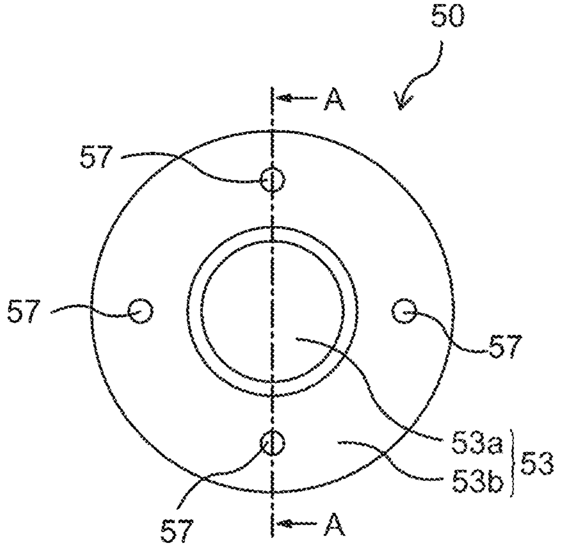
FIGS. 5A and 5B are each a diagram for schematically explaining an example of the medical rubber part according to one or more embodiments of the present disclosure.
Figure 5B:
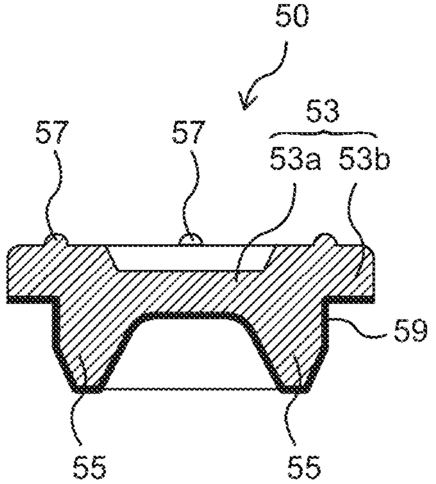

FIGS. 5A and 5B are each a diagram for explaining an example of a medical plug to which one or more embodiments of the present disclosure can be applied. More specifically, a rubber plug for a vial will be explained. FIG. 5A is a plan view, and FIG. 5B is a cross-sectional view at a line A-A in FIG. 5A.

The medical plug 50 can have or consist of: a top plate 53; and a cylindrical leg portion 55 extending downward from the lower surface of the top plate 53. The top plate 53 and the leg portion 55 each can be made from the elastic material. The leg portion 55 can be fitted into a port portion of a medical container when the medical container is plugged with the medical plug according to one or more embodiments of the present disclosure. In FIG. 5B, the cylindrical leg portion 55 can have opposed inner surfaces formed in a tapered shape such that the distance between the inner surfaces of the leg portion gradually decreases from the lower side toward the upper side (upper surface side).

The top plate 53 can have a circular shape in a plan view. The top plate 53 can include or consist of: a piercing portion 53*a* capable of being pierced by an injection needle of an injector; and a flange portion 53*b* which can be, when the medical container is plugged with the medical plug, brought into contact with the upper rim surface of the port portion of the medical container.

Projections 57 for preventing close contact with another rubber plug may be provided on the upper surface side of the flange portion 53*b*.

The piercing portion 53*a* can be a region, of the top plate 53, in which the injection needle is inserted in order to suction a drug solution inside the container. The piercing portion 53*a* can have a circular shape in a plan view and is present at the center of the top plate 53. The piercing portion 53*a* can be formed in a shape recessed from the upper surface.

In the mode in FIGS. 5A and 5B, an inactive resin film 59 can be stacked on the entireties of the lower surface of the top plate 53 and the surface of the leg portion 55. Alternatively, the inactive resin film 59 may be stacked on at least portions of the lower surface of the top plate 53 and the surface of the leg portion 55. As the inactive resin film 59, a polytetrafluoroethylene film may be preferable.

Figure 6A:
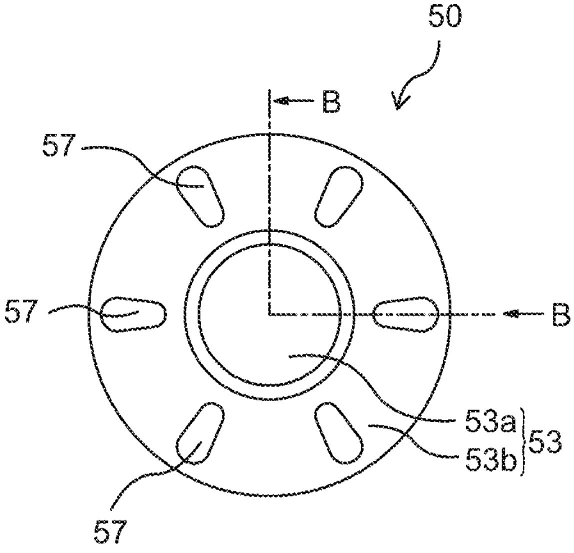
FIGS. 6A and 6B are each a diagram for schematically explaining an example of the medical rubber part according to one or more embodiments of the present disclosure.
Figure 6B:
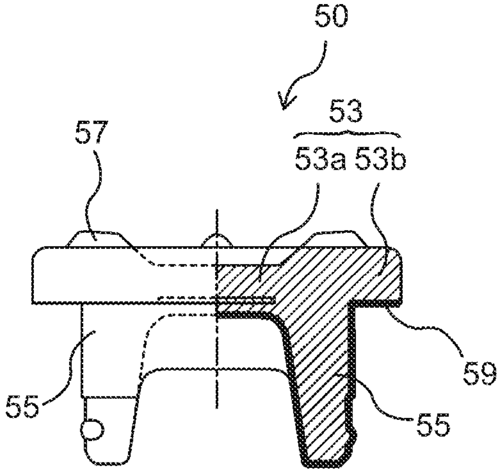

FIGS. 6A and 6B are each a diagram for explaining another mode of the medical rubber plug 50 to which one or more embodiments of the present disclosure can be applied. FIG. 6A is a plan view, and FIG. 6B is a cross-sectional view at a line B-B in FIG. 6A. Descriptions about portions, of the medical rubber plug 50 in FIGS. 6A and 6B, that share the configurations of the corresponding portions in FIGS. 5A and 5B, will be omitted.

The medical rubber plug 50 in the present mode can includes leg portion 55 in the forms of two branching portions extending from the lower surface of the top plate 53. In FIG. 6B, the leg portions 55 in the forms of two branching portions can have opposed inner surfaces formed in a tapered shape such that the distance between the inner surfaces of the leg portions gradually decreases from the lower side toward the upper side (upper surface side). In the mode in FIGS. 6A and 6B, the top plate 53 and the leg portions 55 can each be made from the elastic material, and the inactive resin film 59 can be stacked on the entireties of the lower surface of the top plate 53 and the surfaces of the leg portions 55. Alternatively, the inactive resin film 59 may be stacked on at least portions of the lower surface of the top plate 53 and the surfaces of the leg portions 55.

A nylon film layer may be provided on an upper surface portion of the top plate 53 of either of the medical rubber plugs 50 in FIGS. 5A and 5B and FIGS. 6A and 6B. If a nylon film layer is provided on the upper surface portion of the medical rubber plug 50, mechanical transportability at the time of manufacturing of a pharmaceutical agent can be guaranteed. In addition, if a nylon film layer is provided on the upper surface portion of the medical rubber plug 50, the surface slipperiness of the upper surface portion can be increased, and fragments resulting from needle piercing can be prevented from being generated at the time of piercing with an injection needle.

<Rubber Plug for Vacuum Blood Collection Tube>

Figure 7:
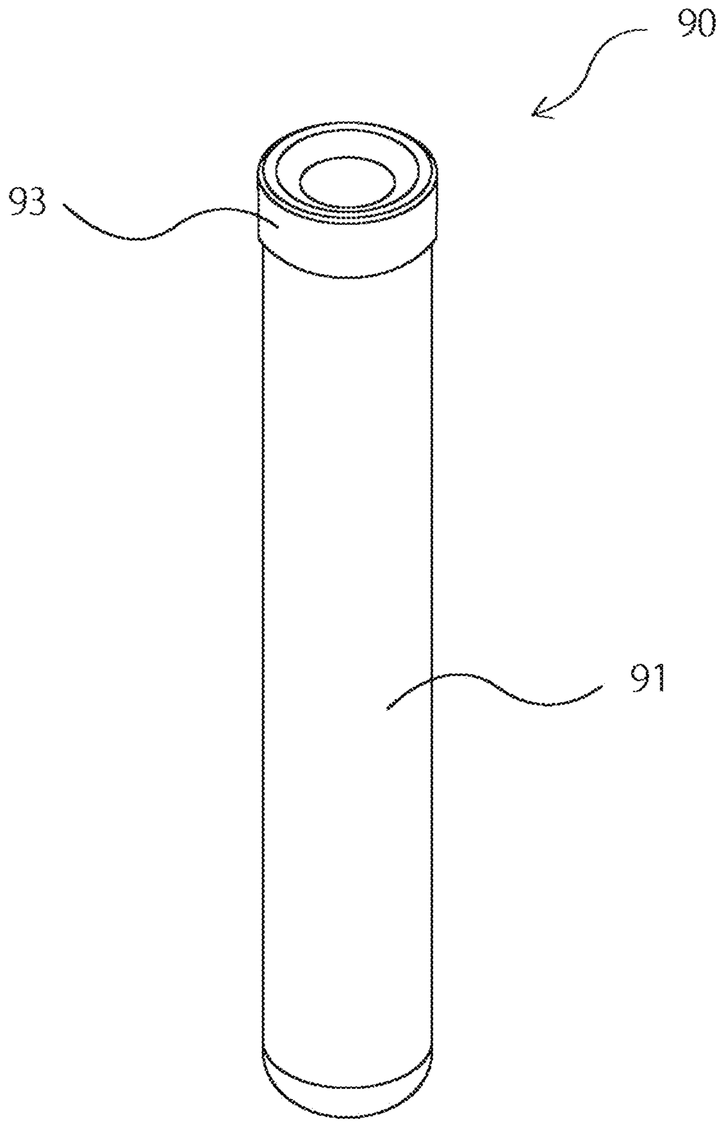
FIG. 7 is a diagram for schematically explaining an example of the medical rubber part according to one or more embodiments of the present disclosure.

FIG. 7 is a diagram for explaining an example of a vacuum blood collection tube according to one or more embodiments of the present disclosure. A vacuum blood collection tube 90 can be composed of or can consist of: a tube 91 having a bottom; and a rubber plug 93 which closes an opening of the tube 91 having the bottom. The vacuum blood collection tube 90 can be configured such that blood can be automatically collected by decompressing the inside of the blood collection tube.

Figure 8A:
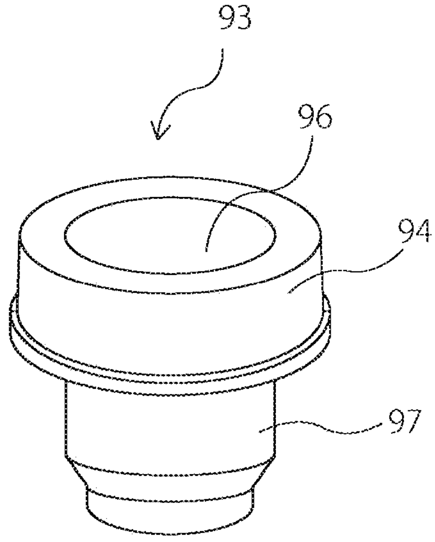
FIGS. 8A and 8B are each a diagram for schematically explaining an example of the medical rubber part according to one or more embodiments of the present disclosure.
Figure 8B:
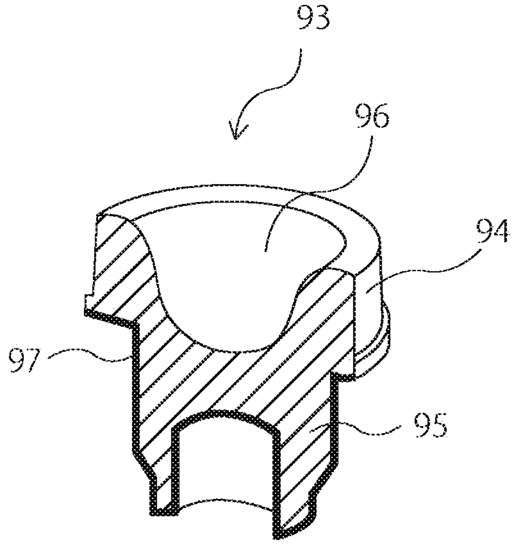

FIGS. 8A and 8B are each a diagram for explaining an example of the medical plug to which one or more embodiments of the present disclosure can be applied. FIGS. 8A and 8B are each a diagram for explaining an example of a rubber plug for the vacuum blood collection tube. FIG. 8A is a perspective view, and FIG. 8B is a cross-sectional view. The rubber plug for the vacuum blood collection tube can include or consist of: a top plate 94; and a cylindrical leg portion 95 extending downward from the lower surface of the top plate 94. The top plate 94 and the leg portion 95 each can be made from the elastic material. When the vacuum blood collection tube is plugged with the rubber plug, the leg portion 95 can be fitted into a port portion of the vacuum blood collection tube. The center of the top plate 94 can be provided with a piercing portion 96 as a region in which an injection needle is inserted. The piercing portion 96 can be formed in a shape recessed from the upper surface. An inactive resin film 97 can be stacked on the entireties of the lower surface of the top plate 94 and the surface of the leg portion 95. Alternatively, the inactive resin film 97 may be stacked on at least portions of the lower surface of the top plate 94 and the surface of the leg portion 95.

<Nozzle Cap>

Figure 9A:
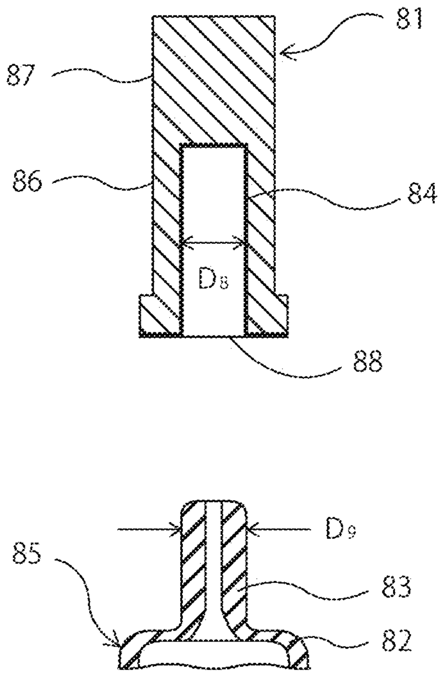
FIGS. 9A and 9B are each a diagram for schematically explaining an example of the medical rubber part according to one or more embodiments of the present disclosure.
Figure 9B:
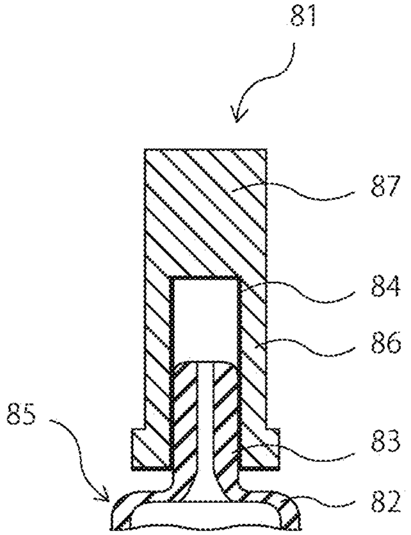

FIG. 9A is a cross-sectional view showing an example of a nozzle cap for a medical syringe and a syringe barrel nozzle to be capped with the nozzle cap according to one or more embodiments of the present disclosure. FIG. 9B is a cross-sectional view showing a state where the nozzle is capped with the nozzle cap. A nozzle cap 81 is integrally formed from the medical rubber composition. The nozzle cap 81 can include or consist of: a tubular portion 86 having an inner diameter D8 that is slightly smaller than an outer diameter D9 of a nozzle 83; and a needle piercing portion 87 formed so as to be contiguous with a one-end side (the upper-end side in the drawings) of the tubular portion 86. The needle piercing portion 87 can be formed in a pillar shape so as to have an outer surface contiguous with the tubular portion 86. The other-end side (the lower end side in the drawings) of the tubular portion 86 can be provided with an opening 88 through which the nozzle 83 is inserted into the tubular portion 86 so that the nozzle 83 can be capped with the nozzle cap 81. An inactive resin film 84 can be stacked on the inner surface of the nozzle cap 81 and the surface of a lower end portion of the tubular portion 86.

Examples

Hereinafter, one or more embodiments of the present disclosure will be described in detail by means of examples, but embodiments of the present disclosure are not limited to the following examples, and any of modifications and implementation modes made within the scope of the gist of the present disclosure is included in the scope of the present disclosure.

[Evaluation Methods]

(1) Eluting-Substance Test

Measurement sample: in a state where each of plunger stoppers as a medical rubber part was put into a polyethylene bag (in either of the packaging modes shown in FIG. 1 and FIG. 2, and in the corresponding packaging-article internal environment indicated in Table 2), the plunger stopper was irradiated with the gamma ray so as to have an absorbed dose of 25 kGy or 50 kGy, whereby a plunger stopper having been irradiated with the gamma ray was obtained.

The measurement sample was tested according to the method in "Extractable substances" described in "7.03 Test for Rubber Closure for Aqueous Infusions" of the 17th edition of the Japanese Pharmacopoeia. Conditions of passing the test were as follows.

Properties of test solution: colorless and clear

Ultraviolet transmissivity: a transmissivity being not lower than 99.0% at each of a wavelength of 430 nm and a wavelength of 650 nm with a layer length of 10 mm Ultraviolet absorption spectrum: an absorbance being not higher than 0.20 at a wavelength of 220 nm to 350 nm pH: the difference between the test solution and a blank test solution being not larger than 1.0

Zinc: the absorbance of a sample solution being not higher than the absorbance of a standard solution Potassium permanganate reducing substance: not higher than 2.0 mL/100 mL (according to a standard in the Japanese Pharmacopoeia)

Post-evaporation residue: not larger than 2.0 mg

If any of these conditions was not satisfied, the measurement sample was evaluated as "Not pass". Meanwhile, if all of the conditions were satisfied, the measurement sample was evaluated as "Pass".

(2) TOC Test

Regarding the eluting liquid in "(1)", a total organic carbon value TOC (NPOC: a TOC obtained through acidification-aeration treatment) was measured.

Measurement analysis device: a Shimadzu total organic carbon analyzer TOC-VCSH (of a combustion oxidizing type)

Measurement analysis condition: a combustion tube temperature being 680 degrees with use of a high-sensitivity catalyst Carrier gas: highly purified air at 150 mL/min.

Injection amount: 200 μL

Concentration of added acid: 1.5%

Aeration treatment time: 90 sec.

The difference between the TOC values before and after irradiation with the gamma ray is indicated. A smaller difference means a smaller extent of deterioration of the eluting performance.

(Determination Criteria)

A (equivalent to pre-irradiation TOC value): the ATOC value being not larger than 0.1 mg/L B (deteriorated relative to pre-irradiation TOC value): the ATOC value being larger than 0.1 mg/L and not larger than 0.3 mg/L C (significantly deteriorated relative to pre-irradiation TOC value): the ATOC value being larger than 0.3 mg/L (3) Slidability Each of plunger stoppers was inserted into a syringe barrel (1-mL COP resin syringe with an inner diameter of 6.35 mm), and the force required for performing pressing with a plunger at a speed of 100 mm/min., was measured by using a precision universal tester (AG-X (100 kN) manufactured by Shimadzu Corporation). The average value of forces required for sliding over sliding distances of 10 mm to 15 mm was recorded as a sliding resistance (N). The difference (post-irradiation sliding resistance value−pre-irradiation sliding resistance value) between the sliding resistance values (N) before and after irradiation with the gamma ray is indicated. A smaller difference means a smaller extent of deterioration of slidability.

(Determination Criteria)

A: the Δsliding resistance value being not larger than 2 N

B: the Δsliding resistance value being larger than 2 N and not larger than 5 N

C: the Δsliding resistance value being larger than 5 N (4) Drug Solution Sealing Performance (Liquid Leakage Test)

A syringe barrel (1-mL cycloolefin (COP) resin syringe with an inner diameter of 6.35 mm) was plugged with each of plunger stoppers. Then, the syringe barrel was filled with a test solution, and the opposite side thereof was capped. This syringe barrel was stored at rest at 40° C. At each of elapse of one day and elapse of one week from the start of the storing, the plunger stopper was observed by using a video microscope (DVM5000 manufactured by Leica Microsystems Inc.) with the magnification of an objective lens being 50-fold, and whether liquid leakage has occurred or not was ascertained. Ten such products were observed. Among the ten products, products in each of which the test solution went beyond the first rib of the stopper were determined to have experienced liquid leakage, and the number of these products is indicated. As the test solution, a test solution obtained by adding 0.2 g/L of a pigment (methylene blue manufactured by Sigma-Aldrich Japan G.K.) and 1.0 g/L of a surfactant (polysorbate 80 manufactured by NOF CORPORATION) to water was used.

(Determination Criteria)

A (no leakage): the number being 0

B (slight leakage): the number being 1

C (leakage): the number being 2 or more (5) Determination as to Suitability for being Ready-to-Use was Performed as Follows.

If the result of the eluting-substance test was "Pass", the result of the TOC test was B or the more favorable evaluation result, the result of the sliding test was B or the more favorable evaluation result, and the result of the liquid leakage test was B or the more favorable evaluation result, it was determined that suitability for being ready-to-use was attained. Meanwhile, if any one of the evaluation results was unsatisfactory, it was determined that suitability for being ready-to-use was not attained.

[Production of Medical Rubber Parts (Plunger Stoppers for Syringes)]

A rubber composition was prepared by blending components other than the crosslinking component among the components indicated in Table 1, kneading the resultant mixture with use of a 10-L pressurization-type sealed kneader at a filling rate of 75%, aging the kneaded product at room temperature, then, adding the crosslinking component to the kneaded product, and kneading the resultant mixture with use of an open roll. The rubber composition was formed in a sheet shape.

TABLE 1

| | | Medical rubber composition No. 1 |
|---|---|---|
| Ingredient (parts by mass) | Chlorinated isobutylene-isoprene rubber | 100 |
| | Triazine derivative | 1.5 |
| | Talc | 50 |
| | Hydrotalcite | 2 |
| | Magnesium oxide | 3 |
| | Carbon black | 0.5 |
| | Titanium oxide | 3 |

TABLE 1-continued

| | | Medical rubber composition No. 1 |
|---|---|---|
| | Oil | 0.5 |
| Cured product (elastic material) | JIS-A hardness | 45 |
| | Compression set (%) | 15% |

Details of the blending materials used are as follows.

Butylated rubber: HT-1066 (chlorine content: 1.26% by weight) manufactured by Exxon Mobil Corporation Triazine derivative: ZISNET DB manufactured by SANKYO KASEI CO., LTD.

Talc: MISTRON Vapor manufactured by Imerys Specialties Japan Co., Ltd.

Hydrotalcite: ALCAMIZER 1 manufactured by Kyowa Chemical Industry Co., Ltd.

Magnesium oxide: MAGSARAT 150s manufactured by Kyowa Chemical Industry Co., Ltd.

Carbon black: DIABLACK G manufactured by Mitsubishi Chemical Holdings Corporation Titanium oxide: KR-380 manufactured by Titan Kogyo Ltd.

Oil: PW380 manufactured by Idemitsu Kosan Co., Ltd.

An inactive resin film having been subjected to one-surface adhesion treatment was superposed on the rubber sheet, and the resultant laminate was placed on a mold and was molded for 10 minutes at 175° C. by using a vacuum press, to be subjected to vulcanization adhesion. Each of plunger stoppers was formed in a form suitable for a 1-mL COP resin syringe (having a syringe barrel with an inner diameter of 6.35 mm). The inactive resin film was stacked on the entireties of the front end surface and the outer circumferential side surface of a gasket body made from the crosslinked rubber (elastic material). As the inactive resin film, the following film was used.

Modified PTFE

Skived film: the product name "NEW VALFLON" manufactured by VALQUA, LTD., with the film thickness T being 70 μm and with the center-line average surface roughness being 0.11 μm The dimensions of the obtained plunger stopper (see FIG. 4) are as follows.

Number of annular ribs: 3

Ho: 7.0 mm

First rib compression rate: 3.8%

Second rib compression rate: 3.1%

Third rib compression rate: 3.1%

H1: 1.0 mm

H2: 0.5 mm

H3: 0.5 mm 100 plunger stoppers having been obtained in each example were put into a packaging bag and sterilized by being irradiated with the gamma ray at the corresponding oxygen concentration and in the corresponding absorbed dose indicated in Table 2. The eluting-substance test and evaluation regarding TOC and liquid leakage properties were executed on the sterilized stoppers, and the results of the execution are indicated together in Table 2.

TABLE 2

| | | Medical rubber part sterilization No. | | | | | |
|---|---|---|---|---|---|---|---|
| | | 1 | 2 | 3 | 4 | 5 | 6 |
| Before irradiation | Packaging-article internal environment | Oxygen adsorber contained | Nitrogen | Nitrogen | Oxygen adsorber contained | Air | Air |
| | Oxygen concentration in packaging article (%) | 0.1% | 3% | 5% | 0.1% | 21% | 21% |
| Irradiation test | Absorbed dose (kGy) | 25 | 25 | 25 | 50 | 25 | 50 |
| (1) Eluting-substance test | Overall evaluation | Pass | Pass | Pass | Pass | Pass | Pass |
| (2) TOC test | ΔTOC value (mg/L) | 0.02 | 0.10 | 0.25 | 0.09 | 0.40 | 0.76 |
| | Evaluation | A | A | B | A | C | C |
| (3) Sliding test | Δsliding resistance value (N) | 0.8 | 1.3 | 2.5 | 2.8 | 3.3 | 6.8 |
| | Evaluation | A | A | B | B | B | C |
| (4) Liquid leakage test n = 10 | Number of products having experienced liquid leakage one day later | 0/10 | 0/10 | 0/10 | 0/10 | 1/10 | 3/10 |
| | Number of products having experienced liquid leakage one week later | 0/10 | 0/10 | 1/10 | 0/10 | 2/10 | 4/10 |
| | Evaluation result | A | A | B | A | C | C |
| Overall determination as to suitability for being ready-to-use | | Suitable | Suitable | Suitable | Suitable | Unsuitable | Unsuitable |

According to the results indicated in Table 2, non-eluting characteristics are maintained by a sterilization method for a medical rubber part that includes a body made from an elastic material and that includes an inactive resin film stacked on at least a portion of a surface of the body, the sterilization method including irradiating a packaging article for the medical rubber part with gamma ray, the packaging article accommodating a plurality of the medical rubber parts and having an oxygen concentration not higher than 5%. In addition, the inactive resin films did not degrade, and thus medical rubber parts each having excellent slidability and less prone to liquid leakage were obtained.

One or more embodiments of the present disclosure can make it possible to provide a sterilization method for a medical rubber part in which non-eluting characteristics are maintained even after sterilization with gamma ray and with which less troubles occur in a medical product manufacturing process.

Mode (1) of the present disclosure is directed to a sterilization method for a medical rubber part that includes a body made from an elastic material and that includes an inactive resin film stacked on at least a portion of a surface of the body, the sterilization method comprising irradiating a packaging article with gamma ray, the packaging article accommodating a plurality of the medical rubber parts and having an oxygen concentration not higher than 5%.

Mode (2) of the present disclosure is directed to the sterilization method for the medical rubber part, according to mode (1), the sterilization method comprising irradiating a packaging article with the gamma ray, the packaging article having an oxygen concentration not higher than 3%.

Mode (3) of the present disclosure is directed to the sterilization method for the medical rubber part, according to mode (1) or (2), wherein the packaging article having an oxygen concentration not higher than 5% is a packaging article in which nitrogen is sealed.

Mode of the present disclosure is directed to the sterilization method for the medical rubber part, according to mode (1) or (2), wherein the packaging article having an oxygen concentration not higher than 5% is a packaging article in which an oxygen adsorber is sealed.

Mode of the present disclosure is directed to the sterilization method for the medical rubber part, according to any one of modes (1) to (4), the sterilization method comprising performing irradiation with the gamma ray such that an absorbed dose of the gamma ray is not lower than 15 kGy.

Mode of the present disclosure is directed to the sterilization method for the medical rubber part, according to any one of modes (1) to (5), wherein the elastic material is composed of a rubber or a thermoplastic elastomer, has a JIS-A hardness not lower than 30 and not higher than 70, and has a compression set not higher than 20%.

Mode (7) of the present disclosure is directed to the sterilization method for the medical rubber part, according to any one of modes (1) to (6), wherein the inactive resin is polytetrafluoroethylene (PTFE), tetrafluoroethylene-ethylene copolymer, or ultrahigh-molecular-weight polyethylene.

Mode (8) of the present disclosure is directed to the sterilization method for the medical rubber part, according to any one of modes (1) to (7), wherein the inactive resin film has a thickness of 10 μm to 150 μm.

Mode (9) of the present disclosure is directed to the sterilization method for the medical rubber part, according to any one of modes (1) to (8), wherein the medical rubber part is a rubber plug for a vial, a cap or a plunger stopper for a syringe, or a rubber plug for a vacuum blood collection tube.

What is claimed is:

1. A sterilization method for a medical rubber part that includes a body made from an elastic material and that includes an inactive resin film stacked on at least a portion of a surface of the body, the sterilization method comprising:

irradiating a packaging article with gamma ray, the packaging article accommodating a plurality of the medical rubber parts and having an oxygen concentration not higher than 5%, wherein the elastic material is a cured product of a medical rubber composition containing a (a) base polymer containing a halogenated isobutylene-isoprene rubber and a proportion of the halogenated isobutylene-isoprene rubber contained in the (a) base polymer is not lower than 90% by mass.

2. The sterilization method for the medical rubber part, according to claim 1, further comprising irradiating a packaging article with the gamma ray, the packaging article having an oxygen concentration not higher than 3%.

3. The sterilization method for the medical rubber part, according to claim 1, wherein the packaging article having an oxygen concentration not higher than 5% is a packaging article in which nitrogen is sealed.

4. The sterilization method for the medical rubber part, according to claim 1, wherein the packaging article having an oxygen concentration not higher than 5% is a packaging article in which an oxygen adsorber is sealed.

5. The sterilization method for the medical rubber part, according to claim 1, further comprising performing irradiation with the gamma ray such that an absorbed dose of the gamma ray is not lower than 15 kGy.

6. The sterilization method for the medical rubber part, according to claim 1, wherein the elastic material has a JIS-A hardness not lower than 30 and not higher than 70, and has a compression set not higher than 20%.

7. The sterilization method for the medical rubber part, according to claim 1, wherein the inactive resin is polytetrafluoroethylene (PTFE), tetrafluoroethylene-ethylene copolymer, or ultrahigh-molecular-weight polyethylene.

8. The sterilization method for the medical rubber part, according to claim 1, wherein the inactive resin film has a thickness of 10 μm to 150 μm.

9. The sterilization method for the medical rubber part, according to claim 1, wherein the medical rubber part is a rubber plug for a vial, a cap or a plunger stopper for a syringe, or a rubber plug for a vacuum blood collection tube.

10. The sterilization method for the medical rubber part, according to claim 1, wherein the (a) base polymer consists essentially of the halogenated isobutylene-isoprene rubber.

11. The sterilization method for the medical rubber part, according to claim 10, wherein the medical rubber composition contains a triazine derivative as a (b) crosslinking agent.

12. The sterilization method for the medical rubber part, according to claim 11, wherein the (b) crosslinking agent consists essentially of the triazine derivative.

13. The sterilization method for the medical rubber part, according to claim 12, wherein the medical rubber composition contains no vulcanization accelerator.

14. The sterilization method for the medical rubber part, according to claim 12, wherein the triazine derivative includes a compound represented by a formula (1):

(1)

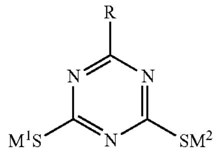

wherein in the formula (1):

R represents —SH, —$OR^1$, —$SR^2$, —$NHR^3$, or —$NR^4R^5$, where $R^1$, $R^2$, $R^3$, $R^4$, and $R^5$ each represent an alkyl group, an alkenyl group, an aryl group, an aralkyl group, an alkylaryl group, or a cycloalkyl group, $M^1$ and $M^2$ each represent H, Na, Li, K, ½Mg, ½Ba, ½Ca, an aliphatic primary, secondary, or tertiary amine, a quaternary ammonium salt, or a phosphonium salt.

15. The sterilization method for the medical rubber part, according to claim 5, wherein the irradiation is performed in a dose that falls within a range of not lower than 1.4 times 25 kGy and not higher than 2.0 times 25 kGy.

* * * * *